US006143088A

United States Patent [19]

Lion et al.

[11] Patent Number: 6,143,088

[45] **Date of Patent: *Nov. 7, 2000**

[54] PERACID-BASED COMPOSITION FOR DECONTAMINATION OF MATERIALS SOILED BY TOXIC AGENTS

[75] Inventors: Claude Lion; Claude Charvy, both of Paris; Gerard Delmas, Malesherbes; Gilbert Magnaud, Vert le Petit, all of France

[73] Assignee: Etat Francais represented by the Delegue General pour l ' Armement, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/952,398

[22] PCT Filed: Feb. 13, 1997

[86] PCT No.: PCT/FR97/00274

§ 371 Date: Feb. 26, 1998

§ 102(e) Date: Feb. 26, 1998

[87] PCT Pub. No.: WO97/33655

PCT Pub. Date: Sep. 18, 1997

[51] Int. Cl.[7] ................................ B08B 3/08; A61L 2/18; C11D 3/39; C11D 3/395

[52] U.S. Cl. .................................... 134/2; 134/3; 134/42; 422/28; 422/37; 252/186.26; 252/186.42; 510/110; 510/310; 510/375; 510/384

[58] Field of Search ......................... 252/186.26, 186.42; 510/110, 175, 310, 370, 375, 384, 391, 535; 422/28, 37; 134/2, 3, 22, 19, 42

[56] References Cited

U.S. PATENT DOCUMENTS

| | | | |
|---|---|---|---|
| 3,353,902 | 11/1967 | Diamond et al. | 8/110 |
| 3,749,673 | 7/1973 | Jones et al. | 510/310 |
| 3,749,674 | 7/1973 | Jones et al. | 510/310 |
| 3,996,152 | 12/1976 | Edwards et al. | 252/186.26 |
| 4,642,198 | 2/1987 | Humphreys et al. | 252/186.26 |
| 4,992,194 | 2/1991 | Liberati et al. | 252/186.26 |
| 5,061,807 | 10/1991 | Gethoffer et al. | 548/473 |

FOREIGN PATENT DOCUMENTS

| | | |
|---|---|---|
| 2651133 | 5/1991 | France . |
| 2676368 | 1/1993 | France . |

OTHER PUBLICATIONS

C.A. Bunton et al., *J. Am. Chem. Soc,* 95, 2912 (1973).

C. Lion et al., *Phosphorus, Sulfur, and Silicon,* 79, 141–145 (1993).

L. Horner et al., *Phosphorus and Sulfur,* 11, 339 (1981).

L. Sepulveda et al., *J. Phys. Chem.,* 89, 5322 (1985).

C. Lion et al., *Bull. Soc. Chem.,* Bel. 99(2), 127–133 (1990).

*Primary Examiner*—Joseph D. Anthony
*Attorney, Agent, or Firm*—Oliff & Berridge, PLC

[57] ABSTRACT

A composition for decontamination of materials soiled by toxic agents, particularly a peracid-based composition for effective decontamination of materials soiled by toxic agents, such as organophosphates and organosulfur compounds. The composition further includes a cationic surfactant.

20 Claims, No Drawings

PERACID-BASED COMPOSITION FOR DECONTAMINATION OF MATERIALS SOILED BY TOXIC AGENTS

This application is the U.S. National Stage application of International Application No. PCT/FR97/00274 filed Feb. 13, 1997.

BACKGROUND OF THE INVENTION

1. Field of the Invention

The present invention relates to a composition intended for decontamination of materials soiled by toxic agents, particularly a peracid-based composition for effective decontamination of materials soiled by toxic agents such as organophosphorous and organosulfur compounds without significantly degrading said materials.

2. Description of Related Art

It is known that various cholinesterase-inhibiting organophosphorous compounds such as organophosphorous, amidophosphates, organoamidophosphates, thiolophosphates, thiolophosphonates, and amidothiolophosphates can be used in agriculture as insecticides and pesticides. On the other hand, certain organosulfur compounds are known as vesicants and used as chemical warfare agents.

Of the best-known organophosphorous compounds used as pesticides or insecticides in agriculture, O,O-diethyl O-p-nitrophenyl phosphate (Paraoxon) and O,O-diethyl O-p-nitrophenyl thiophosphate (Parathion) may be cited, while O-ethyl S-(2-diisopropylaminoethyl)methyl thiolophosphonate (VX) is a well-known chemical warfare agent. These compounds act by irreversibly blocking nerve transmission by forming covalent bonds with acetylcholinesterase, causing death by buildup of acetylcholine in the organism. Another organosulfur compound used as a chemical warfare agent is 2,2'-dichlorodiethyl sulfide (yperite).

If such compounds are used intentionally or accidentally, self-protection is important and it is particularly important to decontaminate the materials with which they have come in contact rapidly and effectively. Hence it is useful to have reagents or compositions able almost instantly to destroy such organophosphorous and organosulfur compounds.

One of the difficulties encountered in practice has to do with the need to avoid degrading the materials to be decontaminated as far as possible. Thus, the most effective compositions currently used in decontamination technology are sodium hydroxide solutions in methyl glycol with diethylamine, or calcium hypochlorite, but these solutions are highly corrosive.

A number of studies have shown that nucleophilic compounds have the properties required for eliminating toxins in the organophosphorous and organosulfur series. C. A. Bunton et al., *J. Am. Chem. Soc.,* 95, 2912 (1973) have shown the properties of the hydroxyl ions for this purpose; other reagents have also been proposed including hydroxamic acids, oximes, mono- and polyphenols, aldehyde hydrates, certain amines, and calcium or sodium hypochlorites.

It has also been proposed that peroxyanions such as anions of hydrogen peroxide, tert-butyl hydroperoxide, perborates, and peracids be used due to their simultaneously nucleophilic and oxidizing properties.

These compounds can be used in compositions also containing surfactants improving contact between the reagent used and the toxin to be eliminated in order to speed up decontamination. In particular, the use of surfactants of the quaternary ammonium type speeds up destruction of toxins by micellar catalysis.

Thus, French patent A-2,651,133 describes compositions made up of solutions containing linear long-carbon-chain peracids with pH values between 6 and 8, generally associated with surfactants such as cetyltrimethylammonium bromide, cetyldimethyl-2-hydroxyethylammonium bromide, cetylmethylbis(2-hydroxyethyl)ammonium bromide, or cetyl-1,4-diazabicyclo(2,2,2)octylammonium bromide. Such compositions destroy Paraoxon, VX, and yperite. However, the peracids used are not commercially available and the stability of the compositions is unsatisfactory.

French patent A-2,676,368 describes aqueous compositions based on magnesium monoperoxyphthalate and a surfactant of the quaternary ammonium salt type useable for decontaminating materials soiled by certain neurotoxic agents such as VX, and vesicants such as yperite.

Destruction of yperite and allied compounds by oxidizers, particularly by potassium monopersulfate, has been described by C. Lion et al., *Phosphorus, Sulfur, and Silicon,* 79, 141–145 (1993), who have shown that the reaction is specific to organosulfur compounds.

Hence, there remains the need to have available compositions capable of effectively and rapidly destroying the aforementioned toxic organophosphorous and organosulfur compounds in order to decontaminate materials soiled by these compounds without degrading them.

SUMMARY OF THE INVENTION

The present invention relates to a composition of the type containing a peracid and a surfactant useable for decontaminating materials contaminated by toxic organophosphorous or organosulfur agents comprising:

a peracid chosen from an imidoperacid represented by general formula (I)

(I)

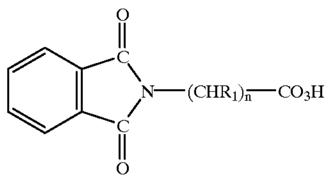

wherein n is a whole number between 2 and 8 and $R_1$ which is a hydrogen atom; and a diperacid represented by general formula (II):

$$HO_3C—(CH_2)_p—CO_3H \quad (II)$$

wherein p is a whole number between 2 and 10;

a cationic surfactant of the quaternary ammonium type.

DETAILED DESCRIPTION OF PREFERRED EMBODIMENTS

According to a preferred embodiment of the invention, the composition is comprised of an aqueous solution with a buffered pH between 8 and 11, preferably between 9 and 10.

In formulas (I) and (II) above, $R_1$ and $R_2$ preferably represent an alkyl group with 1 to 4 carbon atoms, for example a methyl, ethyl, or n-propyl group.

The imidoperacid with general formula (I) can be for example phthalimidoperpropionic or phthalimidopercaproic acid.

The diperacid with general formula (II) can be chosen for example from disperoxydecanedioic, diperazeloic, and diperoxydodecanedioic acids.

The peracids used in the invention are commercially available product or products which can be readily prepared by normal techniques, by the action of hydrogen peroxide in an acid medium (for example in a cold concentrated sulfuric acid medium) on the corresponding acids. A method of preparing such peracids is described by C. Lion et al., *Bull. Soc. Chem, Bel.* 99, (2) 127 (1990).

The cationic surfactant of the quaternary ammonium type is preferably represented by general formula (III):

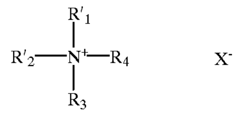

wherein R'$_1$, R'$_2$, and $R_3$, which are identical or different, represent an alkyl or hydroxyalkyl group with 1 to 4 carbon atoms, $R_4$ represents a linear or branched alkyl group with 11 to 18 carbon atoms, and X represents a halogen or a hydroxyl radical.

Of the surfactants represented by general formula (III) above, it is preferable to use those for which $R_1$, $R_2$, and $R_3$ represent a methyl group, an ethyl group, or a hydroxyethyl group, $R_4$ represents a cetyl group, and X is chlorine, bromine, or an —OH radical.

According to one advantageous embodiment of the invention, the surfactant with general formula (III) is chosen from cetyltrimethylammonium bromide or chloride, cetyldimethyl-2-hydroxyethylammonium bromide, cetylmethylbis(2-hydroxyethyl)ammonium bromide, or cetyl-1,4-diazabicyclo(2,2,2)octylammonium bromide.

These surfactants are known and most of them are commercially available. They can be prepared by the methods described by C. A. Bunton et al. (cited above) and by L. Horner et al., *Phosphorus and Sulfur,* 11, 339 (1981). For example, cetyldimethyl-2-hydroxyethylammonium bromide can be obtained by refluxing a solution of hexadecyl bromide and dimethylethanolamine in a mixture of acetonitrile and methanol and recrystallizing the crystals obtained from methanol.

As indicated above, the composition according to the invention is preferably in the form of a buffered aqueous solution with a pH between 8 and 11, preferably between 9 and 10, for example an aqueous solution of a mixture of bicarbonate and sodium hydrogen carbonate.

This aqueous solution is applied to the material to be decontaminated by spraying, atomization, or merely washing, and it is also possible to soak the materials in a bath containing a composition according to the invention.

According to one embodiment of the invention, the peracid and the quaternary ammonium type surfactant, when X is a hydroxyl, can be combined within the same molecule to form a tetraalkylammonium percarboxylate. Such a compound can be obtained by causing the formula (I) or (II) peracid to act on a tetraalkylammonium hydroxide in stoichiometric quantities.

This embodiment is particularly advantageous because the percarboxylate can be generated in situ and is thus in an aqueous solution without the necessity of using a carbonate buffer which in this case is replaced by tetraalkylammonium hydroxide.

The tetraalkylammonium hydroxide can be prepared using the method described by L. Sepulveda et al., *J. Phys. Chem.,* 89, 5322 (1985) from carbon disulfide and sodium ethoxide, and reaction with a tetraalkylammonium bromide in a sulfuric environment, followed by treatment with an alkali such as barium hydroxide.

The effectiveness of the compositions according to the invention for decontamination of materials soiled by toxic organophosphorous or organosulfur compounds was verified by causing them to act on known compounds such as O,O-diethyl o-p-nitrophenyl phosphate (Paraoxon), in the organophosphorous compound series, and 2-phenyl-2'-chlorodiethyl sulfide, an yperite analog, in the organosulfur series.

The tests conducted show that the compositions according to the invention destroy compounds such as Paraoxon and the yperite analog almost instantaneously. This result is obtained with the composition containing the formula (I) or (II) peracid in combination with the quaternary ammonium type surfactant as well as with the composition containing a tetraalkylammonium percarboxylate.

In addition, it is found that the composition according to the invention has excellent stability over time, contrary to classical peracid-based compositions, and is not corrosive to the various materials usually treated.

The following examples. describe in greater detail the destructive effects on Paraoxon and an yperite analog of compositions according to the invention including either a combination of peracid and surfactant (Example 1), or a tetraalkylammonium percarboxylate (Example 2).

The destruction kinetics for Paraoxon are determined by the usual technique at 402 nm with UV spectroscopy corresponding to the absorption peak of the p-nitrophenoxide ion released, at 25° C.

The rates of destruction of the yperite analog referred to above are determined at regular intervals by chromatographic analysis after addition of an inorganic reducing agent (ferrous sulfate) or an organic reducing agent (triphenylphosphine). The pH is 9.

EXAMPLE 1

Table 1 below shows the half-reaction time (in seconds) at 25° C. when each of the four peracids listed below acts on Paraoxon ($5 \times 10^{-5}$ M) in a $2 \times 10^{-3}$ M solution at pH 9.

Peracids used:

1. phthalimidopercaproic acid
2. diperoxydodecanedioic acid
3. diperazeloic acid
4. diperoxydodecanedioic acid The surfactants used in combination with the above peracids are the following:

5. cetyltrimethylammonium chloride
6. cetyltrimethylammonium bromide
7. cetyldimethyl-2-hydroxyethylammonium bromide
8. cetylmethylbis(2-hydroxyethyl)ammonium bromide
9. cetyl-1,4-diazabicyclo(2,2,2)octylammonium bromide

TABLE 1

| | | Surfactant | | | | |
|---|---|---|---|---|---|---|
| Peracid | — | 5 | 6 | 7 | 8 | 9 |
| MMPP | 5300 | 20 | 30 | 50 | 80 | 20 |
| 1 | 27500 | 100 | 100 | 150 | 270 | 60 |
| 2 | 3600 | 10 | 10 | 20 | 30 | 10 |
| 3 | 4100 | 20 | 20 | 40 | 30 | 10 |
| 4 | 10800 | 20 | 10 | 30 | 40 | 50 |

These results show that the composition according to the invention yields results equivalent to those obtained with magnesium monoperphthalate (MMPP) which is the best decontaminant against Paraoxon currently known. In addition, by Example 2 below, the compositions according to the n are just as effective against organosulfur compounds.

Example 2

| Peracid | pH | $T_{1/2}$(s) |
|---|---|---|
| MMPP | 9 | 10 |
| 1 | 10, 5 | 40 |
| 2 | 9, 1 | 10 |
| 3 | 9, 3 | 10 |
| 4 | 9, 6 | 10 |

This example shows that the reaction is practically total in a few seconds. The comparison with MMPP shows the effectiveness of the cetyltrimethylammonium percarboxylate according to the invention.

What is claimed is:

1. A method for decontaminating materials contaminated with toxic organophosphorous or organosulfur agents, comprising:

a) providing a composition consisting essentially of:

(1) a peracid or a salt of said peracid;

(2) optionally, an aqueous solution with a buffered pH of 8 to 11; and (3) a cationic quaternary ammonium type surfactant, wherein said peracid is selected from the group consisting of:

(i) an imidoperacid represented by general formula (I):

(I)

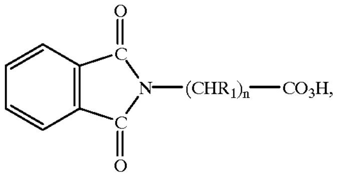

wherein n is a whole number between 2 and 8 and $R_1$ is a hydrogen atom, and (ii) a diperacid represented by general formula (II):

$HO_3C—(CH_2)_p—CO_3H$ (II)

wherein p is a whole number between 2 and 10; and b) contacting a material to be decontaminated with the composition.

2. A method for decontaminating materials contaminated with toxic organophosphorous or organosulfur agents, consisting essentially of:

a) preparing a composition consisting essentially of:

(1) a peracid or a salt of said peracid;

(2) optionally, an aqueous solution with a buffered pH of 8 to 11; and (3) a cationic quaternary ammonium type surfactant, wherein said peracid is selected from the group consisting of:

(i) an imidoperacid represented by general formula (I):

(I)

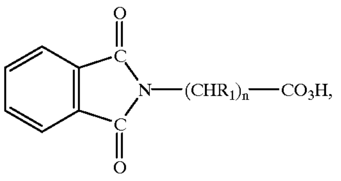

wherein n is a whole number between 2 and 8 and $R_1$ is a hydrogen atom, and (ii) a diperacid represented by general formula (II):

$HO_3C—(CH_2)_p—CO_3H$ (II)

wherein p is a whole number between 2 and 10; and b) placing the composition in contact with a material to be decontaminated.

3. A method for decontaminating materials contaminated with toxic organophosphorous or organosulfur agents, comprising:

a) preparing a composition consisting essentially of:

(1) a peracid or a salt of said peracid;

(2) optionally, an aqueous solution with a buffered pH of 8 to 11; and (3) a cationic quaternary ammonium type surfactant, wherein said peracid is selected from the group consisting of:

(i) an imidoperacid represented by general formula (I):

(I)

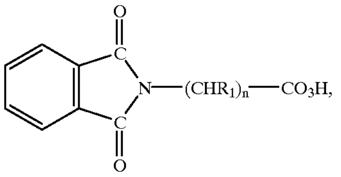

wherein n is a whole number between 2 and 8 and $R_1$ is a hydrogen atom, and (ii) a diperacid represented by general formula (II):

$HO_3C—(CH_2)_p—CO_3H$ (II)

wherein p is a whole number between 2 and 10; and b) placing the composition in contact with a material to be decontaminated.

4. The method of claim 3, wherein the contact step (b) is at room temperature for not more than 270 seconds.

5. The method of claim 3, wherein said peracid is phthalamidoperpropionic or phthalamidopercaproic acid.

6. The method of claim 3, wherein said diperacid is selected from the group consisting of diperoxydecanedioic acid, diperazelaic acid, and diperoxydodecanedioic acid.

7. The method of claim 3, wherein said composition further comprises an aqueous solution with a buffered pH of 8 to 11.

8. The method of claim 3, wherein said composition has a half-reaction time against organophosphorous and organosulfur compounds in a contact time of less than 270 seconds.

9. The method of claim 3, wherein said peracid and said surfactant are combined in equimolar amounts.

10. The method of claim 3, wherein in said step (b) the composition is contacted with the material be a method selected from the group consisting of spraying, atomization, washing and soaking.

11. The method of claim 3, wherein said composition consists of:

said peracid or a salt of said peracid;

said surfactant;

and an optional aqueous solution with a buffered pH of 8 to 11.

12. The method of claim 11, wherein said composition has a half-reaction time against organophosphorous and organosulfur compounds in a contact time of less than 270 seconds.

13. The method of claim 3, wherein said quaternary ammonium surfactant is represented by formula (III):

(III)

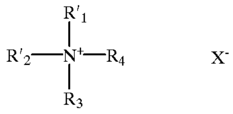

wherein $R'_1$, $R'_2$, and $R_3$, which are identical or different, represent an alkyl or hydroxyalkyl group with 1 to 4 carbon atoms, $R_4$ represents a linear or branched alkyl group with 11 to 18 carbon atoms, and X represents a halogen or a hydroxyl radical.

14. The method of claim 13, wherein said peracid and said surfactant are combined within one molecule to form a tetraalkylammonium percarboxylate, and wherein X represents a hydroxyl radical.

15. The method of claim 14, wherein said composition does not include a separate buffer solution.

16. The method of claim 15, wherein said composition has a half-reaction time against organophosphorous and organosulfur compounds in a contact time of less than 270 seconds.

17. The method of claim 13, wherein said $R'_1$, $R'_2$, and $R_3$ represent a methyl group, an ethyl group, or a hydroxyethyl group, wherein $R_4$ represents a cetyl group, and wherein X is a chlorine, a bromine, or an —OH radical.

18. The method of claim 17, wherein said surfactant is selected from the group consisting of cetyltrimethylammonium bromide, cetyltrimethylammonium chloride, cetyldimethyl-2-hydroxyethylammonium bromide, cetylmethylbis(2-hydroxyethyl)ammonium bromide, and cetyl-1,4-diazabicyclo(2,2,2)octylammonium bromide.

19. The method of claim 17, wherein X is a bromine radical.

20. The method of claim 17, wherein X is an —OH radical.

* * * * *